US009307946B2

(12) United States Patent　(10) Patent No.: US 9,307,946 B2
Cowdery et al.　(45) Date of Patent: Apr. 12, 2016

(54) CEILING MOUNTED MEDICAL IMAGING SYSTEM

(71) Applicant: Dental Imaging Technologies Corporation, Hatfield, PA (US)

(72) Inventors: Frederick W. Cowdery, Perkasie, PA (US); Frank Speranza, Warminster, PA (US); Carl Anthony Yacono, Telford, PA (US); Tyler Betteridge, Oreland, PA (US)

(73) Assignee: DENTAL IMAGING TECHNOLOGIES CORPORATION, Hatfield, PA (US)

( * ) Notice: Subject to any disclaimer, the term of this patent is extended or adjusted under 35 U.S.C. 154(b) by 351 days.

(21) Appl. No.: 13/804,607

(22) Filed: Mar. 14, 2013

(65) Prior Publication Data

US 2014/0270062 A1　Sep. 18, 2014

(51) Int. Cl.
　*A61B 6/00*　(2006.01)
　*A61B 6/14*　(2006.01)
(52) U.S. Cl.
　CPC .............. *A61B 6/4464* (2013.01); *A61B 6/4435* (2013.01); *A61B 6/14* (2013.01); *A61B 6/466* (2013.01); *A61B 6/467* (2013.01)
(58) Field of Classification Search
　CPC ........ A61B 6/14; A61B 6/025; A61B 6/4233; A61B 6/4441; A61B 6/4452; A61B 6/4464; A61B 6/466; A61B 6/467; A61B 6/4435; A61B 6/4458; H05G 1/02
　USPC ............... 378/5, 6, 8, 12, 21, 35, 38, 39, 122, 378/193, 197
See application file for complete search history.

(56) References Cited

U.S. PATENT DOCUMENTS 3,118,066 A * 1/1964 Thomas et al. ............... 378/194
3,244,883 A * 4/1966 Labus et al. .................. 378/194
4,435,830 A　3/1984 Suzuki et al.
(Continued)

FOREIGN PATENT DOCUMENTS

JP　　63211599　　9/1988
KR　　2010043334　　4/2010
(Continued)

OTHER PUBLICATIONS

Extended European Search Report for European Application No. 14159663, dated Sep. 4, 2014 (7 pages).

*Primary Examiner* — Glen Kao
*Assistant Examiner* — Julio M Duarte-Carvajalino
(74) *Attorney, Agent, or Firm* — Michael Best & Friedrich LLP

(57) ABSTRACT

A medical imaging device mountable on a support structure having a horizontal surface and at least one substantially vertical surface. The imaging device includes a frame and a gantry having a radiation source and a radiation detector. The gantry is rotatable with respect to the frame. The imaging device includes a first vertical adjustment element and a second vertical adjustment element. The first vertical adjustment element has a first end couplable to the horizontal surface and a second end coupled to the frame, the first end is located a first distance from the second end, and adjustable over a first range. The second vertical adjustment element has a third end coupled to the frame and a fourth end coupled to the gantry. The third end is located a second distance from the fourth end, and is adjustable over a second range, and the fourth end is rotatable with respect to the third end.

15 Claims, 8 Drawing Sheets

(56) References Cited

U.S. PATENT DOCUMENTS

| | | |
|---|---|---|
| 4,868,845 A | 9/1989 | Koropp |
| 5,050,204 A | 9/1991 | Siczek et al. |
| 5,086,447 A | 2/1992 | Siczek et al. |
| 5,155,757 A | 10/1992 | Sakaniwa et al. |
| 5,226,069 A * | 7/1993 | Narita ............................ 378/197 |
| 5,533,090 A * | 7/1996 | Nyzen ............................ 378/197 |
| 5,602,889 A | 2/1997 | Oldendorf et al. |
| 5,740,227 A | 4/1998 | Kusch |
| 5,870,450 A | 2/1999 | Khutoryansky et al. |
| 6,155,713 A | 12/2000 | Watanabe |
| 6,241,387 B1 | 6/2001 | Will |
| 6,461,039 B1 | 10/2002 | Klotz et al. |
| 6,496,558 B2 | 12/2002 | Graumann |
| 6,742,929 B2 | 6/2004 | Horbaschek |
| 6,764,217 B2 | 7/2004 | Yasuda et al. |
| 6,869,217 B2 | 3/2005 | Rasche et al. |
| 6,872,000 B2 | 3/2005 | Atzinger |
| 7,018,097 B2 | 3/2006 | Schmitt |
| 7,182,511 B2 | 2/2007 | Boomgaarden |
| 7,452,130 B2 | 11/2008 | Molz et al. |
| 7,478,949 B2 | 1/2009 | Niessen et al. |
| 7,500,783 B2 | 3/2009 | Kalender |
| 7,534,036 B2 | 5/2009 | Delmas et al. |
| 7,559,691 B2 | 7/2009 | Fuhrmann |
| 7,591,588 B2 | 9/2009 | Rainer |
| 7,616,983 B2 | 11/2009 | Nekovar et al. |
| 7,635,221 B2 | 12/2009 | Spahn |
| 7,641,391 B2 | 1/2010 | Schwieker |
| 7,695,192 B2 | 4/2010 | Henderson et al. |
| 7,744,277 B2 | 6/2010 | Noda et al. |
| 7,755,058 B2 | 7/2010 | Maschke |
| 7,770,860 B1 | 8/2010 | Culpepper et al. |
| 7,796,732 B2 | 9/2010 | Huang |
| 7,804,933 B2 | 9/2010 | Nyholm |
| 7,804,938 B2 | 9/2010 | Lin et al. |
| 7,832,927 B2 | 11/2010 | Dyreby et al. |
| 7,839,976 B2 | 11/2010 | Haupl et al. |
| 7,857,511 B2 | 12/2010 | Hesl et al. |
| 7,874,729 B2 | 1/2011 | Okuno et al. |
| 7,914,206 B2 | 3/2011 | Diez |
| 2003/0112926 A1 | 6/2003 | Atzinger |
| 2004/0008820 A1 | 1/2004 | Schmitt |
| 2005/0220273 A1 | 10/2005 | Ueffinger |
| 2007/0140436 A1 | 6/2007 | Perry et al. |
| 2008/0069304 A1 | 3/2008 | Muszak et al. |
| 2008/0116351 A1 | 5/2008 | Dave et al. |
| 2009/0257561 A1 * | 10/2009 | Okuno et al. .................. 378/116 |
| 2011/0075814 A1 | 3/2011 | Bose et al. |

FOREIGN PATENT DOCUMENTS

| | | |
|---|---|---|
| WO | 8703795 | 7/1987 |
| WO | 2011064449 | 6/2011 |
| WO | 2011070227 | 6/2011 |

* cited by examiner

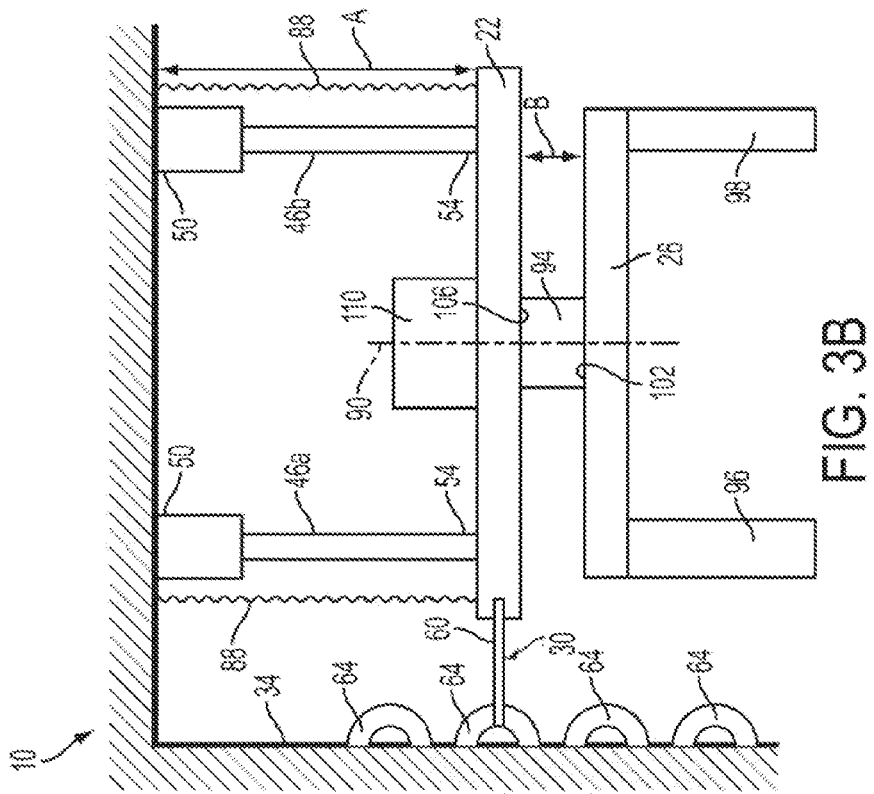
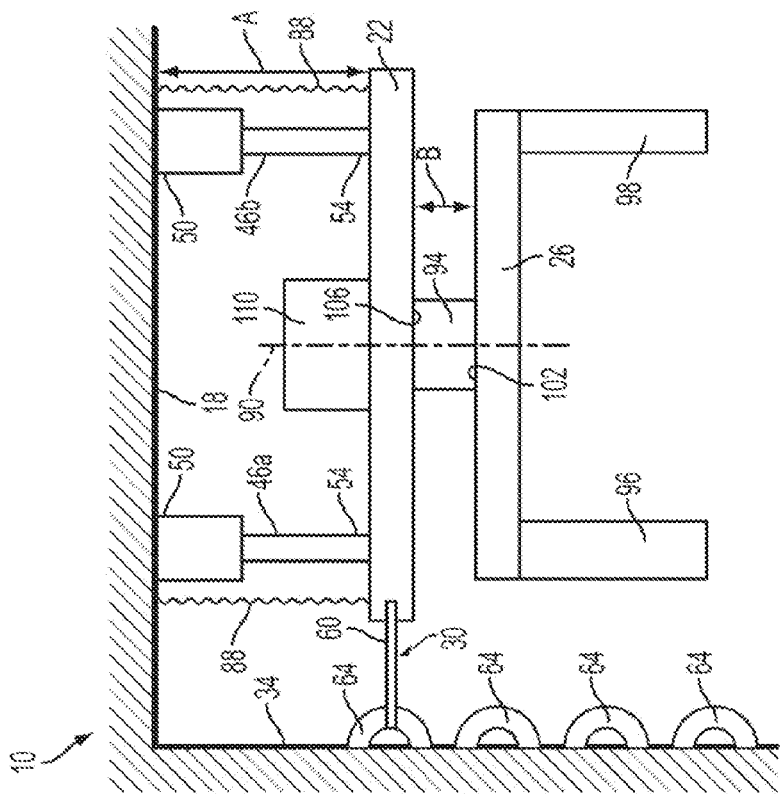

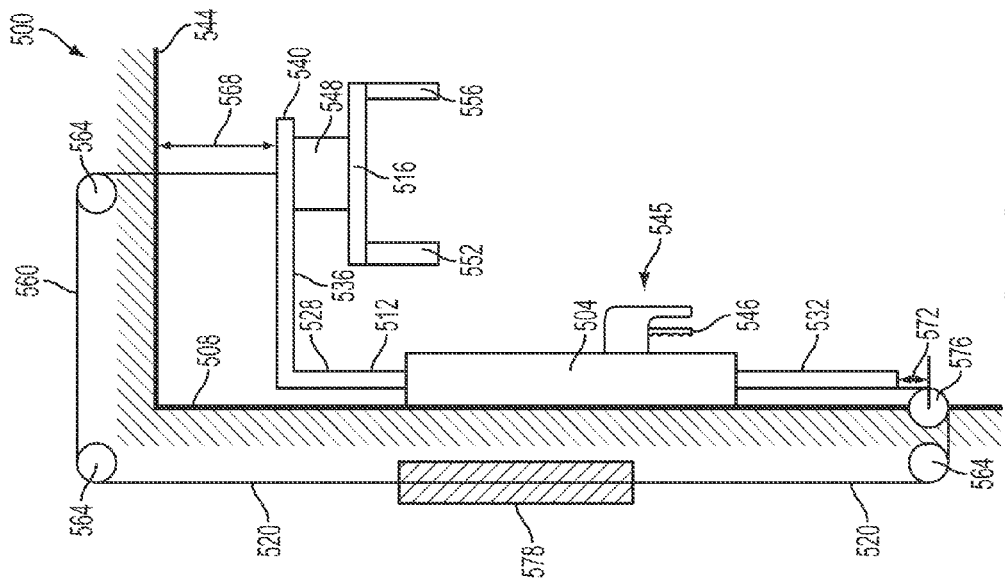
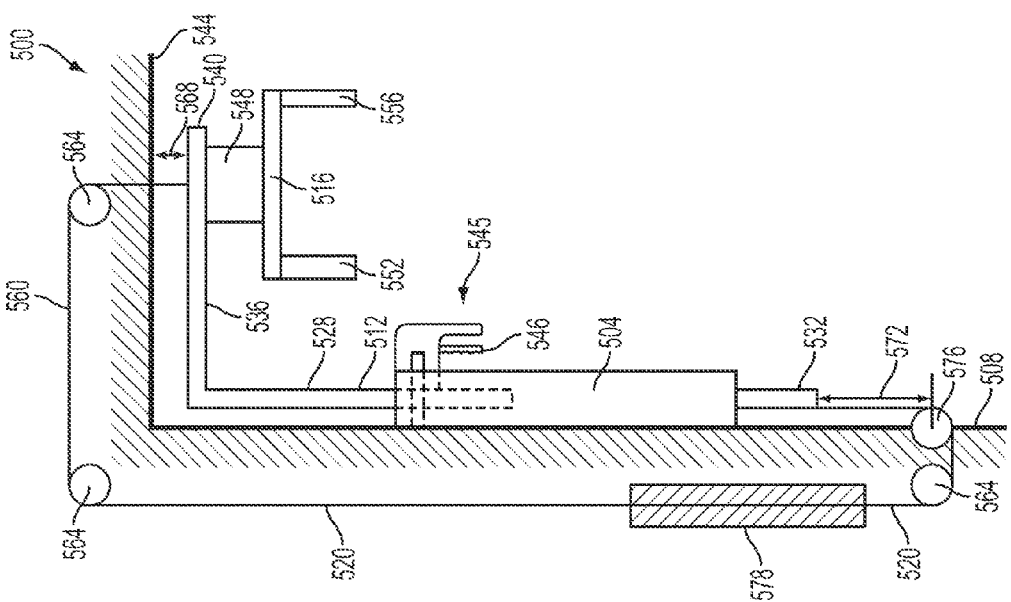

CEILING MOUNTED MEDICAL IMAGING SYSTEM

TECHNICAL FIELD

Embodiments of the invention relate to ceiling mounted medical imaging systems, such as dental imaging systems.

BACKGROUND

Medical imaging devices are capable of performing a variety of different types of imaging (e.g., radiography, magnetic resonance imaging ("MRI"), computed tomography ("CT"), etc.). For dental imaging systems, such as a conventional dental CT system, a patient often sits upright in a tomography device and an x-ray source and detector are rotated about the patient. The x-ray source and the detector are each mounted to a gantry of the tomography device.

SUMMARY

2D Panoramic and 3D Cone Beam Dental X-ray products have become an important tool in many dental offices. However, they are often times very large and consume vast amounts of valuable floor and wall space. A major selling point for dental imaging machines is the image quality, which in turn is at least partially determined by the distance between the radiation detector and the radiation source of the rotating gantry. Unfortunately, to accommodate the larger distances, many high quality units require a base that occupies 16 or more square feet of office floor space. Furthermore, the size and orientations that the patients while imaging is taking place is limited by the size of the bases of these devices. This can be exacerbated by patients using wide wheelchairs and the like.

In light of the deficiencies and limitations of existing imaging devices, the invention described herein relates to an imaging device having a gantry assembly that is configured to be mounted to a ceiling or other elevated, substantially horizontal surface. By mounting the gantry assembly from the ceiling, the present invention minimizes the amount of floor space that must be used to support the imaging device, and as a result allows for a more efficient use of the office space available. The present invention also allows for more flexibility when accommodating patients in unique sizes or orientations, such as patients in wheelchairs.

In one embodiment, the invention provides a medical imaging device. The device is mountable on a support structure having a horizontal surface and at least one substantially vertical surface. The imaging device includes a frame, a gantry, a first vertical adjustment element, and a second vertical adjustment element. The gantry has a radiation source and a radiation detector. The first vertical adjustment element has a first end couplable to the horizontal surface and a second end coupled to the frame, the first end is located a first distance from the second end, and adjustable over a first range. The second vertical adjustment element has a third end coupled to the frame and a fourth end coupled to the gantry. The third end is located a second distance from the fourth end, and is adjustable over a second range smaller than the first range, and the fourth end is rotatable with respect to the third end.

In another embodiment, the invention provides a medical imaging device mountable on a support structure having a horizontal surface and at least one vertical surface. The imaging device includes a mount, a substantially L-shaped frame, a gantry, and a cable. The mount is couplable to the vertical surface. The frame is coupled to the mount for relative vertical movement thereto, and has a first leg and a second leg. The gantry is rotatably mounted on the first leg, and includes a radiation source and a radiation detector. The cable extends between the first leg and the horizontal surface, and is configured to at least partially support a load created by the frame and gantry.

In another embodiment, the invention provides a medical imaging device mountable on a stationary support structure having a horizontal surface and a vertical surface. The vertical surface has multiple vertically spaced rungs thereon. The medical imaging device includes a frame, a lateral support arm, and a gantry. The frame is couplable to the horizontal surface for relative vertical movement thereto. The lateral support arm is coupled to the frame and configured to engage with a corresponding one of the vertically spaced rungs to maintain the horizontal position of the frame with respect to the vertical surface. The gantry is coupled to the frame for relative rotational movement thereto, and includes a radiation source and a radiation detector.

In another embodiment, the invention provides a medical imaging device mountable to a horizontal surface. The medical imaging device includes a frame, a gantry an adjustment element, and a lateral support. The frame is coupled to and vertically moveable with respect to the horizontal surface. The gantry has a radiation source and a radiation detector. The adjustment element adjusts the vertical position of the gantry with respect to the frame, and has a first end coupled to the gantry and a second end coupled to the frame. The first end is located a first distance from the second end and the first distance is adjustable over a first range. The first end is also rotatable with respect to the second end. The lateral support element maintains a horizontal alignment in response to rotation of the first end with respect to the second end.

Other aspects of the invention will become apparent by consideration of the detailed description and accompanying drawings.

BRIEF DESCRIPTION OF THE DRAWINGS

FIGS. 3a and 3b illustrate the gantry assembly of FIG. 2 with a first vertical adjustment element in various positions, the gantry assembly having one embodiment of a lateral support assembly.

FIGS. 6a-c illustrate another embodiment of a medical imaging system.

DETAILED DESCRIPTION

Figure 1:
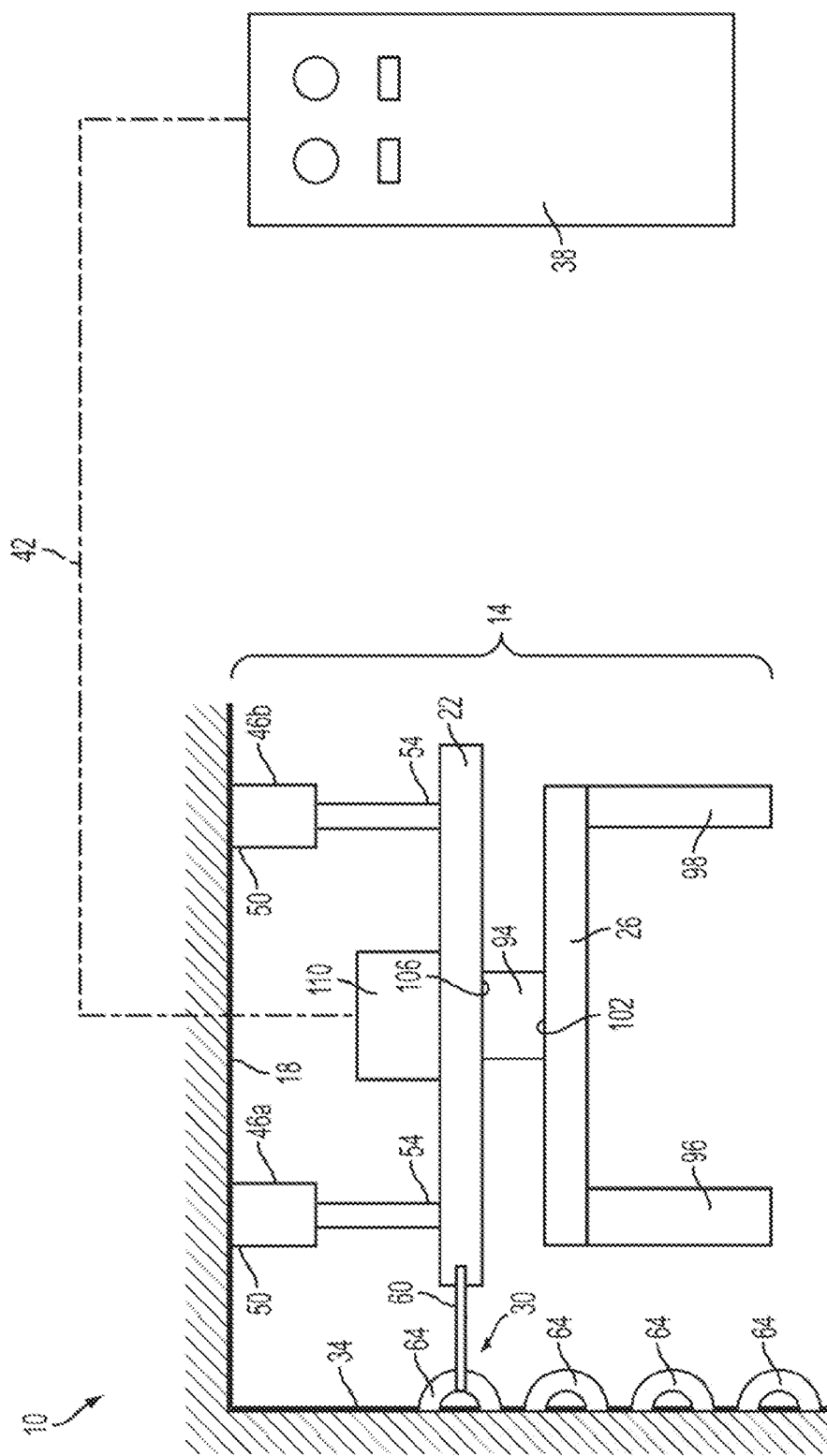
FIG. 1 illustrates is a perspective view of one embodiment of a medical imaging system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

FIGS. 1-5b illustrate one embodiment of a medical imaging system 10 having a gantry assembly 14 mountable to a ceiling or other elevated horizontal surface 18. The medical imaging system 10 of the present invention is provided to reduce the amount of floor space occupied by similar floor mounted imaging systems that regularly require a large footprint base (usually greater than 16 square feet) to provide the stabilization required to produce a quality image.

Furthermore, the present invention includes a two-step vertical adjustment system providing increased flexibility to compensate for patients of different shapes, sizes and imaging orientations. The two-step system allows the present invention to accommodate various patient orientations (e.g., standing, sitting), as well as oversized wheelchairs.

In the illustrated construction, the gantry assembly 14 of the medical imaging system 10 includes a frame 22, a gantry 26 adjustably coupled to the frame 22 for rotation with respect thereto, and a lateral support assembly 30 couplable to a vertical surface or wall 34.

The medical imaging device 10 also includes an electronics enclosure 38 (e.g., a control station) formed separately from and located away from the gantry assembly 14. The electronics enclosure 38 contains the inputs and power supplies necessary for controlling and powering the gantry assembly 14. The electronics enclosure 38 is positioned away from the gantry assembly 14, such as in a closet, a hallway, and the like, to further help minimize the amount of floor space occupied by the system 10. To minimize tripping hazards, the electronics enclosure 38 is electrically coupled to the gantry assembly 14 via a wiring harness (e.g., an electrical harness) or conduit 42 routed through the ceiling 18. The separate electronics enclosure 38 allows the present invention to be shipped more cheaply and easily than comparable floor mounted units.

Illustrated in FIGS. 1, and 2-5b, the frame 22 of the medical imaging system 10 is a substantially rigid element coupled to and vertically moveable over a first range with respect to the ceiling 18 (e.g., varying distance A). The frame 22 is moveable between a first position (see FIG. 3a), where the frame 22 is a first distance from the ceiling 18, and a second position (see FIG. 3b), where the frame 22 is a second distance from the ceiling 18. When assembled, the frame 22 is coupled to the ceiling 18 by way of a first vertical adjustment element 46 extending therebetween (described below). The frame 22 is formed from a rigid material, such as metal stock or plate, able to withstand the weight of the gantry 26 without warping or weakening.

Illustrated in FIGS. 1, and 2-5b, the first vertical adjustment element 46 extends between the ceiling 18 and the frame 22. The first vertical adjustment element 46 generally includes two members 46a, 46b, each having a first end 50 coupled to the ceiling 18, and a second end 54 coupled to the frame 22. During use, the overall length of each member can be adjusted (e.g., via commands from the electronics enclosure 38) to vary the distance between the frame 22 and the ceiling 18 over a first range. In the illustrated construction, each vertical support element 46a, 46b comprises a linear actuator. To assure the assembly 14 is secure, each vertical adjustment element 46a, 46b is coupled to a ceiling joist or other rigid support element within the ceiling.

Illustrated in FIGS. 2-5b, the lateral support assembly 30 extends between the frame 22 and the wall 34 to minimize image distortion due to vibrations produced by the gantry 26 during use. More specifically, the lateral support assembly 30 acts as a stabilizing mechanism, maintaining the horizontal position of the frame 22 with respect to the wall.

Figure 2:
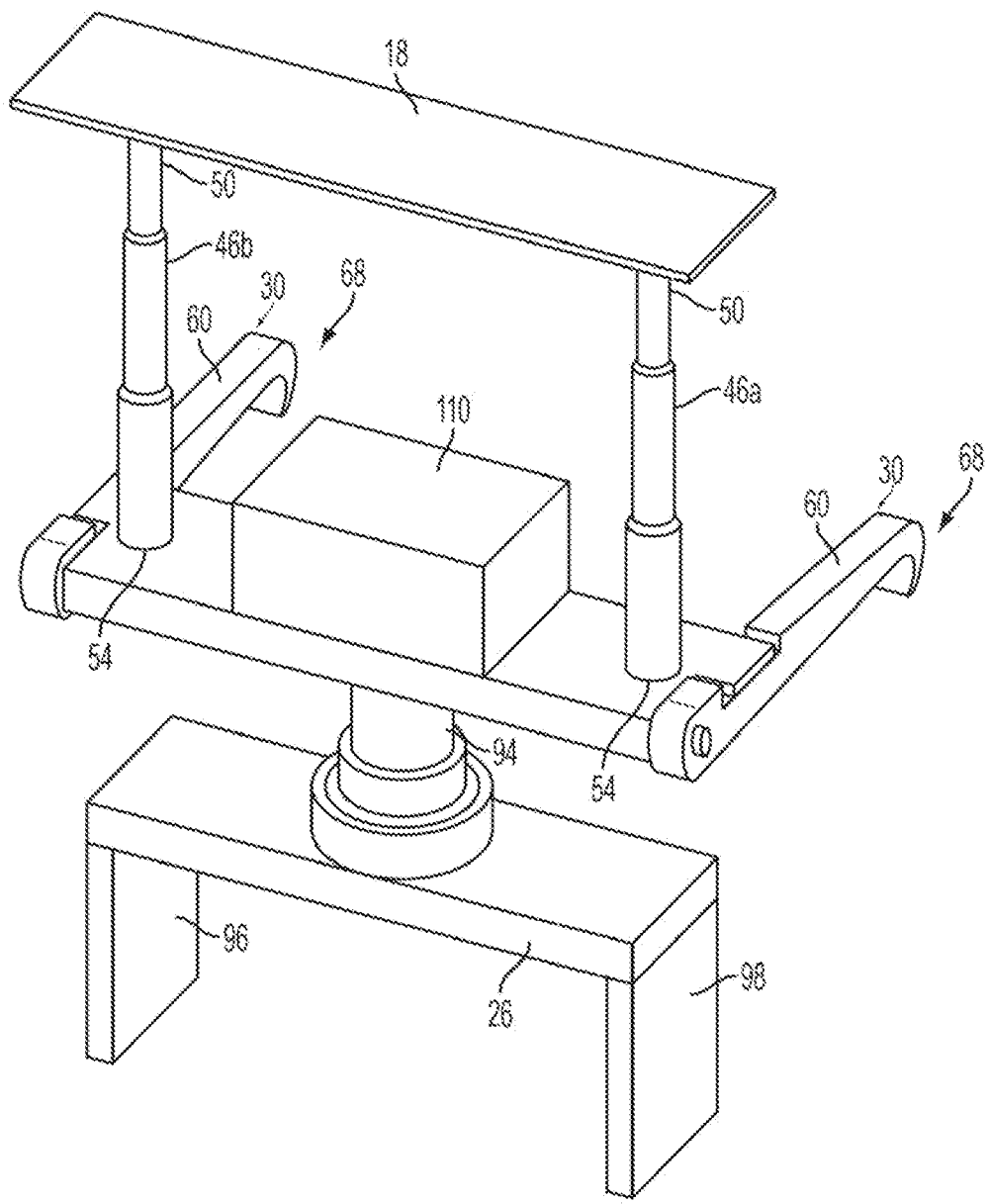
FIG. 2 illustrates the gantry assembly of the medical imaging system of FIG. 1.

FIGS. 2, 3a and 3b illustrate one embodiment of the lateral support assembly 30 having a lateral support member 60 and a plurality of vertically spaced rungs 64 coupled to the wall 34. During use, the lateral support member 60 is coupled to a corresponding one of the vertically spaced rungs 64 to secure the frame 22 thereto. In the illustrated construction, each rung 64 is anchored at even intervals along the height of the wall 34. The rungs 64 may include a loop, bar, hook, and the like.

Figure 2A:
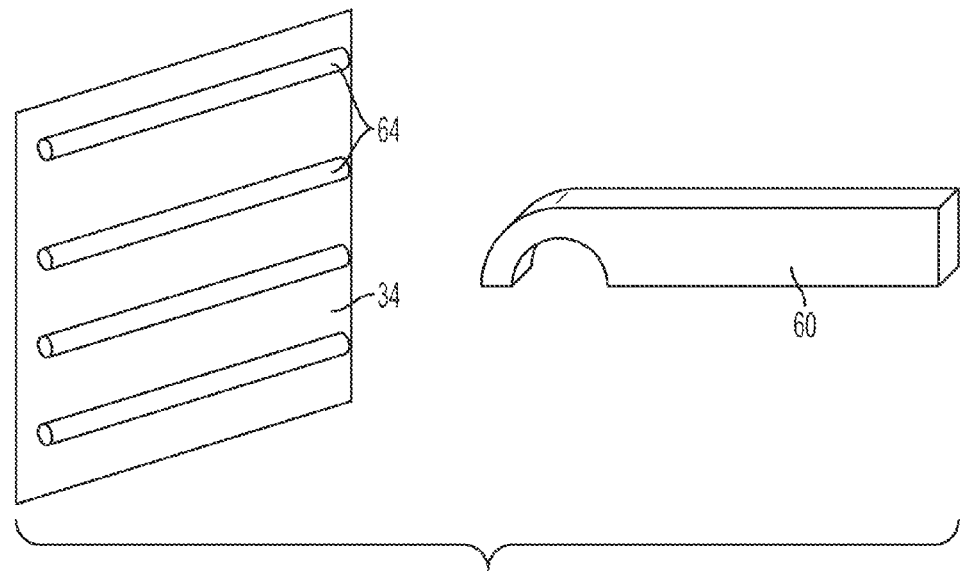
FIGS. 2a and 2b illustrate exemplary embodiments of lateral support mechanisms or assemblies for the gantry assembly shown in FIG. 2.
Figure 2B:
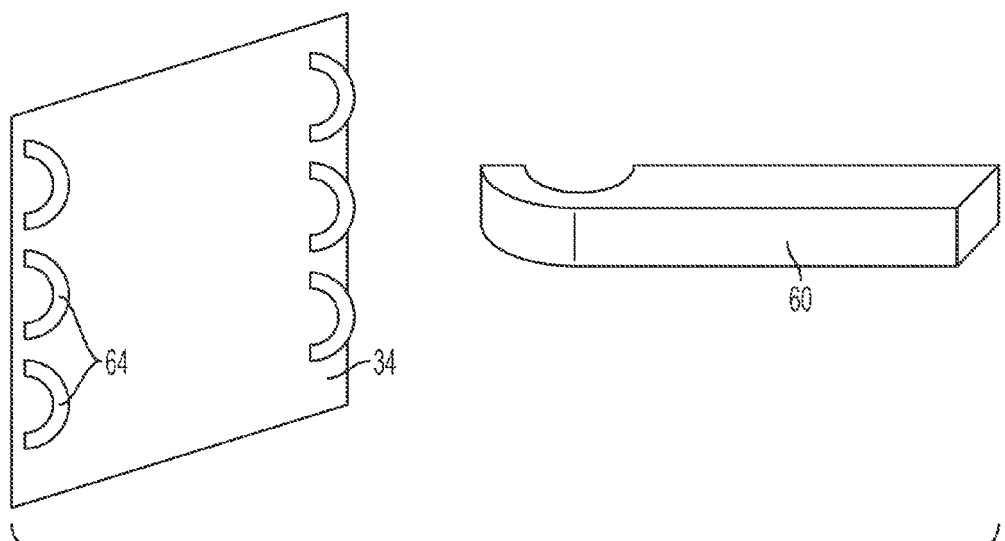

The lateral support member 60 of the present invention includes a substantially rigid bar having a hooked end 68 opposite the end coupled to the frame 22 (see FIG. 2). During use, the operator adjusts the vertical height of the frame 22 with respect to the ceiling 18 until the desired height is achieved. The user then couples the hooked end 68 to the rung 64 substantially corresponding to the height of the frame 22 at that time (see FIGS. 3a and 3b). Once coupled, the lateral support member 60 maintains the horizontal position of the frame 22 with respect to the wall 34. In some embodiments, the lateral support assembly 30 may include horizontal rungs 64 with vertically oriented support member 60 (see FIG. 2a). In other embodiments the lateral support assembly 30 may include vertical rungs 64 with horizontally oriented support members 60 (see FIG. 2b).

To readjust the height of the frame 22 for a new patient, the user de-couples the support member 60 from the rung 64, adjusts the height of the frame 22 as necessary, and then re-couples the support member 60 to a different rung 64 corresponding to the new vertical height of the frame 22.

Since the lateral support member 60 is most effective when oriented horizontally (e.g., the frame 22 is vertically aligned with the rung 64), the distance between the rungs 64 can at least partially dictate the "coarseness" of the movement of the frame 22. As such, the distance between adjacent rungs 64 is less than the range of a second vertical adjustment member 94 (described below) to assure all vertical positions can be accommodated by the gantry 26.

Figure 4B:
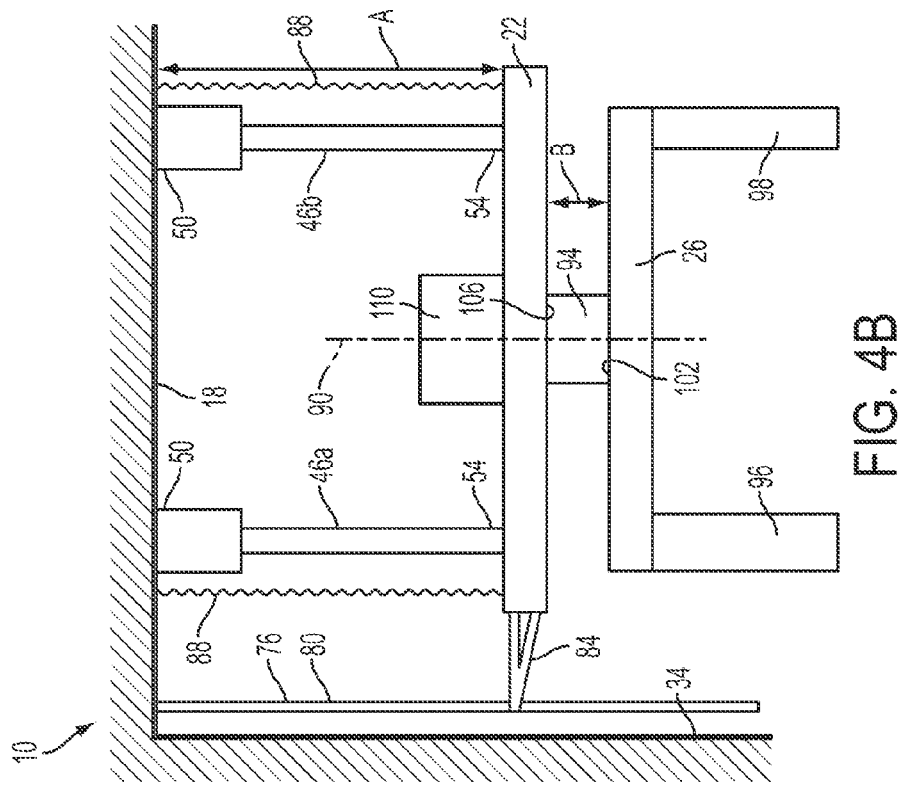
FIGS. 4a and 4b illustrate the gantry assembly of FIG. 2 with the first vertical adjustment elements in various positions, the medical imaging device having another embodiment of a lateral support assembly.
Figure 4A:
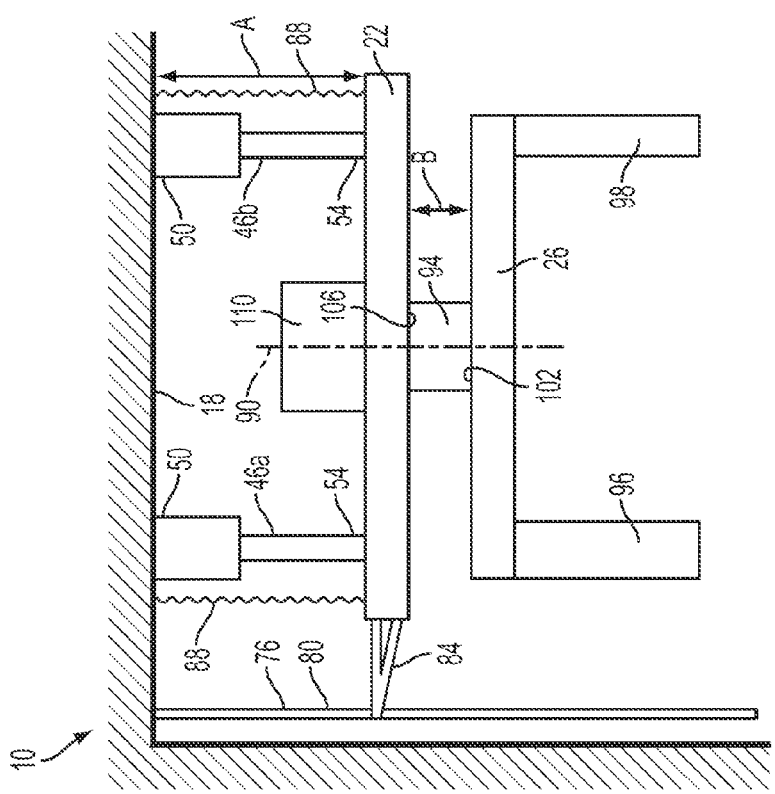
Figure 5A:
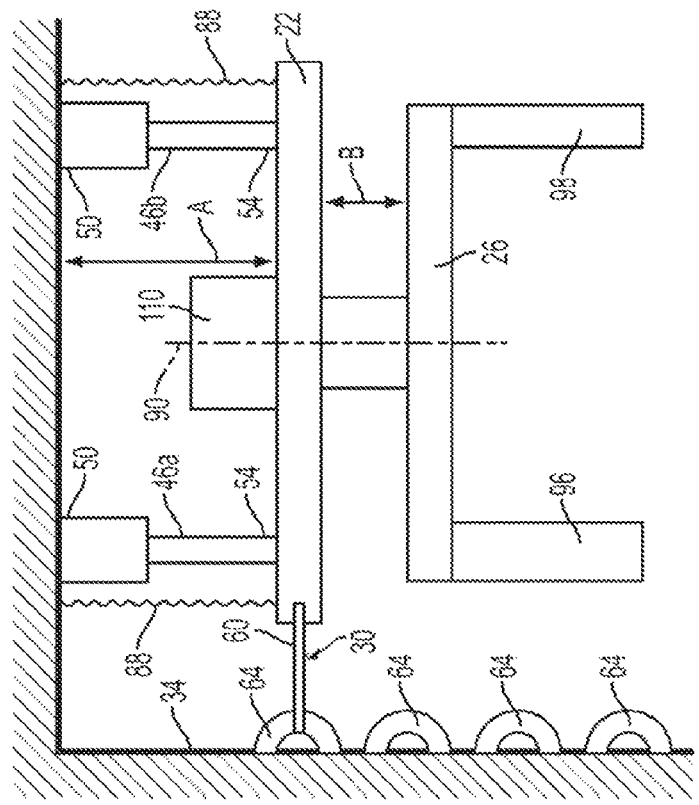
FIGS. 5a and 5b illustrate the gantry assembly of FIG. 2 with a second vertical adjustment element in various positions.
Figure 5B:
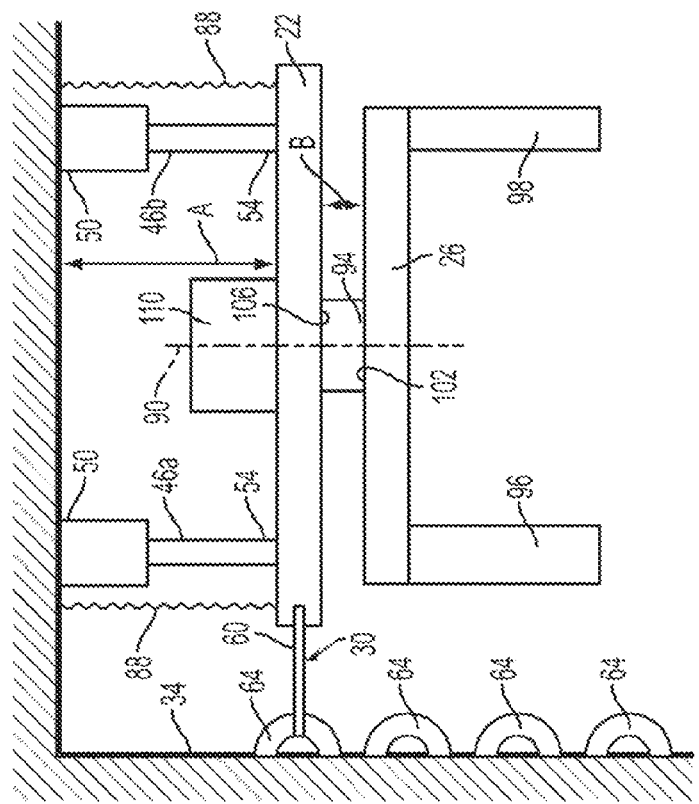

FIGS. 4a and 4b illustrate another embodiment of a lateral support assembly 76 including a vertically oriented track 80 coupled to the wall 34, and a bracket 84 coupled to the track 80 and moveable with respect thereto. The bracket 84 is coupled to the track 80 such that it can move vertically along the length of the track 80 but not horizontally. Therefore, when the frame 22 is adjusted vertically with respect to the ceiling 18, the bracket 84 travels along the track 80 while continuously maintaining the horizontal position of the gantry assembly 22. In some constructions, the bracket 84 may also include a stop or brake (not shown) to secure the frame 22 in a particular vertical position.

The gantry assembly 14 also includes a pair of security cables 88 (i.e., safety members) extending between the frame 22 and the ceiling 18. Each cable 88 is of sufficient length to allow the frame 22 to move the full range of positions and is strong enough to bear the weight of the frame 22, gantry 26, and other elements of the gantry assembly 14. If a failure should occur, (e.g., the first vertical adjustment elements 46 detach or break) the frame 22 would only fall a short distance before being stopped by the cables 88.

Illustrated in FIGS. 1-5b, the gantry 26 is coupled to the frame 22 for vertical and rotation movement with respect thereto about an axis 90. When assembled, the gantry 26 is coupled to the frame 22 with a second vertical adjustment element 94 (described below) movable independently of the first vertical adjustment element 46. The gantry 26 includes a radiation source 96 and a radiation detector 98, each positioned opposite and facing one another. During use, the radiation source 96 and radiation detector 98 work in tandem to produce 2D or 3D images of the patient as is well known in the art.

The second vertical adjustment element 94 includes a first end 102 coupled to the gantry 26, and a second end 106 coupled to the frame 22. The length of the second vertical adjustment element 94 is adjustable over a second range between a first vertical position (see FIG. 5a), where the gantry 26 is a first vertical distance from the frame 22, and a second vertical position (see FIG. 5b), where the gantry 26 is a second vertical distance from the frame 22. The first end 102 is also rotatable with respect to the second end 106 allowing the gantry 26 to rotate with respect to the remainder of the gantry assembly 14 (e.g., to produce 3D images). In the illustrated embodiment, the rotation of the gantry 26 is driven by a gear box 110 located on the frame 22. In the illustrated construction, the second vertical adjustment element 94 is adjustable over a smaller range than the first vertical adjustment element 46.

To use the imaging device 10, the operator first places the patient below the gantry assembly 14 so that the patient's head is substantially aligned with the axis 90 of the gantry 26. Dependent upon the specifics of the image to be taken and the physical condition of the patient, the patient may be placed in a number of positions (e.g., seated, standing, or in a wheelchair).

Using the controls on the electronics enclosure 38, the operator coarsely adjusts the vertical position of the frame 22 (and as a result the remainder of the gantry 26) by altering the length first vertical adjustment elements 46a, 46b. Once the frame is aligned with a rung 64 that is closely aligned with the patient's head, the operator couples the lateral support element 60 to the corresponding rung 64 on the wall 34, securing the frame 22 thereto. If the track 80 embodiment of the lateral support assembly 30 is in use, the operator may engage the stop on the bracket 84 if one is present.

The operator then finely adjusts the vertical position of the gantry 26 by altering the length of the second vertical adjustment element 94. Once in position (e.g., the radiation source 96 and the radiation detector 98 are vertically aligned with the patient's head), the user can begin the imaging process as is well known in the art. In the instances where a 3D image is required, the user may also activate the gearbox 110 to cause the gantry 26 to rotate around the user's head about axis 90.

When the imaging process is complete, the operator can reverse the above process to raise the gantry assembly 14 up and out of the way, allowing for full use of the office floor and wall space.

Figure 6A:
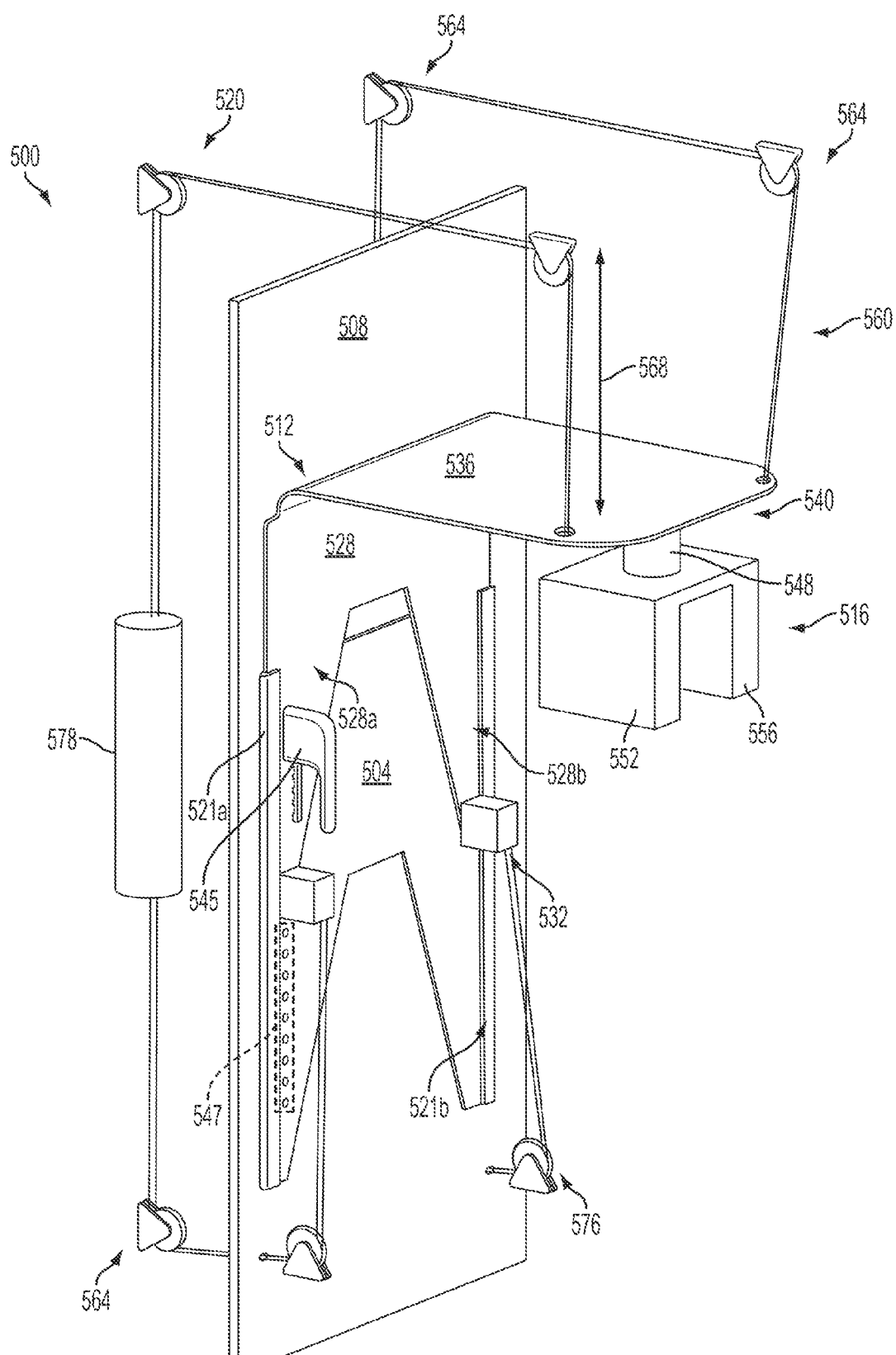

FIGS. 6a-6c illustrate another embodiment of an imaging assembly 500, with FIG. 6a showing a perspective view and FIGS. 6b and 6c showing side views. The second embodiment of the imager assembly 500 includes a mount 504 couplable to a substantially vertical wall 508, a frame 512 adjustable with respect to the mount 504, a gantry 516 mounted on the frame 512, and a support assembly 520. Similar to the imaging assembly 10 described above, the imaging assembly 500 is designed to minimize the amount of floor space occupied while maintaining image quality.

The mount 504 of the imaging assembly 500 comprises a pair of brackets 521a,b, each coupled to the wall 508 and configured to sliding receive at least a portion of the frame 512 therein. During use, the mount 504 is configured to allow the frame 512 to move vertically with respect thereto while restricting lateral movement relative to the wall 508.

The frame 512 of the imaging assembly 500 is substantially "L" shaped having a first leg 528 with a first end 532, and a second leg 536 with a second end 540. As shown in FIG. 6a, the first leg 528 may further include a cutaway forming two prongs 528a,b, each terminating at first ends 532. When assembled, the first leg 528 of the frame 512 is at least partially received and moveable within the mount 504 to vertically adjust the position of the second leg 536 with respect to the ceiling 544 (see FIGS. 6a and 6b). The first leg 528 further includes a release/engage handle 545, also referred to as a lock, to allow the user to adjust and secure the vertical position of the frame 512 with respect to the mount 504. The handle 545 includes, for instance a spring-loaded trigger 546 coupled to a projection of the handle 545 that selectively engages a hole or indent 547 on the mount 504. When the trigger 546 is depressed and the projection disengaged from the holes 547, vertical adjustment of the frame 512 is enabled. Upon releasing the trigger 546, the projection of the handle 545 moves back towards and engages one of the holes 547, locking the frame 512 into vertical position.

The second leg 536 of the frame 512 extends substantially perpendicularly outward from the top of the first leg 528. The second leg 536 extends outward to produce the second end 540, which in turn acts as a mounting point for the gantry 516.

The gantry 516 of the imager assembly 500 is coupled to the second end 540 of the second leg 536 of the frame 512, and held a fixed distance from the wall 508. The gantry 516 is coupled to the second end 540 of the frame 512 by a rotation assembly 548. During operation of the imaging assembly 500 the operator may choose to rotate the gantry 516 with respect to the frame 512 to produce 3D images. Similar to the gantry 26 described above, the gantry 516 includes a radiation source 552 and a radiation detector 556, each positioned substantially opposite from and facing one another. During operation of the imaging assembly 500, the detector 556 and the source 552 work in tandem to create the desired images of the patient.

Although the present invention is described as containing a rotation assembly 548, in alternate constructions, the gantry 516 may be coupled to the second end 540 of the frame 512 by a device similar to the second vertical adjustment element 94 described above, allowing the gantry 516 to be both vertically adjustable and rotatable relative to the frame 512.

The imaging assembly 500 also includes a support assembly 520 to at least partially support the weight of the gantry 516 regardless the position of the frame 512 with respect to the mount 504. In the illustrated construction, the support assembly 520 includes a cable 560 originating at the second end 540 of the second leg 536, extending over one or more support elements or pullies 564 and a base pulley 576, and terminating at the first end(s) 532 of the first leg 528. When assembled, the support assembly 520 produces a support length 568, extending between the second end 540 and the ceiling 544, and an anchor length 572 extending between the first end 532 and the base pulley 576. When the first leg 528 is locked in the mount 504 to fix the height of the gantry, the support assembly 520 exerts tension between the first and second legs 528 and 536, thus maintaining the angle between them and preventing the frame 512 from sagging, bending, or collapsing.

During operation, the support assembly 520 is oriented to accommodate for any vertical movement of the frame 512 with respect to the mount 504. For example, if the frame 512 is moved vertically upwards one unit, the support length 568 will become one unit shorter while the anchor length 572 will become one unit longer. Since the remainder of the cable supports 564 remain stationary, the overall length of the cable pathway remains constant and the cable 560 continues to at least partially support the weight of the gantry 516 (see FIG. 6b). In contrast, if the frame 512 is moved vertically downward one unit, the anchor length 572 will decrease one unit while the support length 568 will increase one unit, again maintaining the overall length of the cable pathway (see FIG. 6c). Therefore, the cable 560 essentially transmits any forces exerted onto the second end 540 through itself and onto the first end 532, creating the desired supporting effect.

As illustrated, the support assembly 520 further includes a counterweight 578 secured along each cable 560. Accordingly, a constant tension is exerted onto the second end 540, regardless of the position of the frame 512. In alternate embodiments, the cables 560 do not include counterweights 578, but similarly extend from the second end 540, over one or more support elements 564 and the base pulley 576, to the first end(s) 532 of the frame 512.

What is claimed is:

1. A medical imaging device mountable on a support structure having a horizontal surface and at least one substantially vertical surface, the imaging device comprising:
   a frame;
   a gantry having an X-ray radiation source and a radiation detector, and wherein the gantry is rotatable with respect to the frame;
   a first vertical adjustment element having a first end coupleable to the horizontal surface and a second end coupled to the frame, the first end located a first distance from the second end, and wherein the first vertical adjustment element is configured such that the first distance is adjustable over a first range;
   a second vertical adjustment element having a third end coupled to the frame and a fourth end coupled to the gantry, the third end located a second distance from the fourth end, wherein the second vertical adjustment element is configured so that the second distance is adjustable over a second range; and
   a horizontal support member to maintain a horizontal position of the frame with respect to the vertical surface, the horizontal support member including a bracket extending from the frame and coupleable with a corresponding rung of a plurality of vertically spaced rungs mounted on the vertical surface.

2. The medical imaging device of claim 1, wherein the second range is smaller than the first range.

3. The medical imaging device of claim 1, wherein the first vertical adjustment element comprises a linear actuator.

4. The medical imaging device of claim 1, further comprising a safety member extending between the horizontal surface and the frame.

5. The medical imaging device of claim 4, wherein the safety member comprises a cable.

6. The medical imaging device of claim 1, wherein the frame and gantry form a gantry assembly, and wherein the imaging device further includes a control station separate from the gantry assembly.

7. The medical imaging device of claim 6, wherein the gantry assembly and the control station are joined by an electrical harness.

8. A medical imaging device mountable on a support structure having a horizontal surface and at least one vertical surface, the imaging device comprising:
   a mount coupleable to the vertical surface;
   a substantially L-shaped frame coupled to the mount for relative vertical movement thereto, wherein the vertical movement is parallel to the vertical surface, and the L-shaped frame having a first leg and a second leg;
   a gantry rotatably mounted on the first leg, the gantry having an X-ray radiation source and a radiation detector; and
   a cable extending between the first leg and the horizontal surface, the cable configured to at least partially support a load created by the frame and gantry.

9. The medical imaging device of claim 8, further comprising one or more support elements coupled to at least one of the horizontal surface and the vertical surface.

10. The medical imaging device of claim 9, wherein the cable includes a first end coupled to the first leg, a second end coupled to the second leg, and a body passing over the support elements.

11. The medical imaging device of claim 9, wherein the one or more support elements comprises one or more pulleys.

12. The medical imaging device of claim 8, wherein the cable includes a first portion extending between the first leg and the horizontal surface and a second portion extending between the second leg and a support element fixedly coupled to the vertical surface.

13. The medical imaging device of claim 12, wherein when a length of the first portion increases a length of the second portion decreases an equal amount.

14. A medical imaging device mountable on a stationary support structure having a horizontal surface and a vertical surface, the vertical surface having multiple vertically spaced rungs thereon, the medical imaging device comprising:
   a frame coupleable to the horizontal surface for relative vertical movement thereto;
   a lateral support arm coupled to the frame and configured to engage with a corresponding one of the vertically spaced rungs to maintain a horizontal or angular position of the frame with respect to the vertical surface; and
   a gantry coupled to the frame for relative rotational movement thereto, the gantry having an X-ray radiation source and a radiation detector.

15. The medical imaging device of claim 14, wherein the gantry is coupled to the frame for relative vertical and rotational movement thereto.

* * * * *